United States Patent [19]

Tessier et al.

[11] Patent Number: 4,565,822

[45] Date of Patent: Jan. 21, 1986

[54] 2-FLUORO-2-CYANOETHENYL CYCLOPROPANE CARBOXYLATES AS PESTICIDES

[75] Inventors: Jean Tessier, Vincennes; André Teche; Pierre Girault, both of Paris, all of France

[73] Assignee: Roussel Uclaf, Paris, France

[21] Appl. No.: 637,106

[22] Filed: Aug. 2, 1984

[30] Foreign Application Priority Data

Aug. 4, 1983 [FR] France .............................. 83 12858
Jan. 19, 1984 [FR] France .............................. 84 00798

[51] Int. Cl.$^4$ ................... C07D 213/65; C07C 121/48; A01N 53/00
[52] U.S. Cl. ..................................... 514/351; 514/471; 514/520; 514/525; 514/514; 260/465 D; 260/465.4; 546/300; 549/496
[58] Field of Search ................... 260/465 D, 465.4; 424/263, 285, 304; 546/300; 549/496; 514/351, 471, 520, 525, 514

[56] References Cited

U.S. PATENT DOCUMENTS 4,385,070  5/1983  Bentley et al. .................. 260/465 D

FOREIGN PATENT DOCUMENTS 0033259  8/1981  European Pat. Off. ............ 562/506
48409    9/1984  European Pat. Off. ............ 560/124
2099810  12/1982  United Kingdom .

Primary Examiner—Henry R. Jiles
Assistant Examiner—Dale A. Bjorkman
Attorney, Agent, or Firm—Bierman, Peroff & Muserlian

[57] ABSTRACT

Novel cyclopropanecarboxylates in all possible isomeric forms or mixtures thereof of the formula

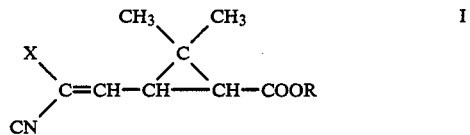

with a 1R,cis or 1R,trans structure and wherein X is a halogen, R is selected from the group consisting of (A) optionally unsaturated alkyl of 2 to 12 carbon atoms, (B) optionally unsaturated cycloalkyl of 3 to 12 carbon atoms, (c)

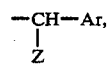

Z is selected from the group consisting of —C≡CH, —CH$_3$ and —CN and Ar is selected from the group consisting of —C$_6$H$_5$, —C$_6$F$_5$,

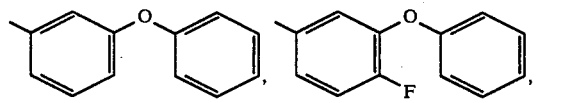

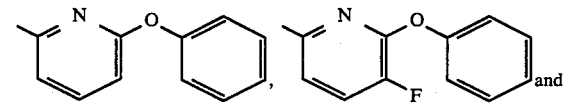

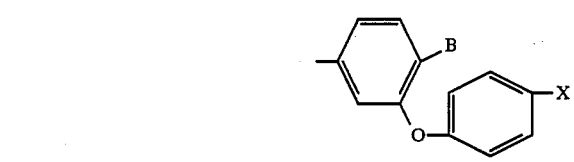

B is hydrogen or fluorine and X is fluorine, chlorine or bromine

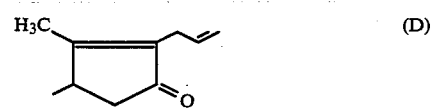

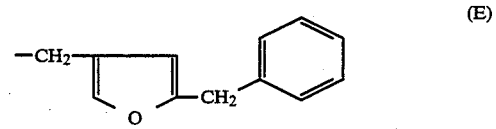

and

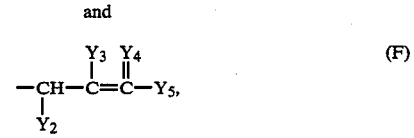

$Y_2$ is selected from the group consisting of hydrogen, fluorine, chlorine bromine, —C≡N and —C≡CH, $Y_3$, $Y_4$, and $Y_5$ are individually selected from the group consisting of hydrogen, fluorine, chlorine, bromine alkyl of 1 to 8 carbon atoms and cycloalkyl of 3 to 8 carbon atoms optionally substituted by one or more functional groups, alkenyl of 2 to 8 carbon atoms and alkynyl of 2 to 8 carbon atoms, and two of $Y_3$, $Y_4$ and $Y_5$ can form rings between them with the proviso that if X is bromine and R is

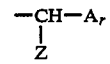

and Z is cyano or ethynyl and $A_r$ is

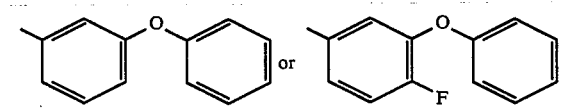

the carbon carrying Z is in the (S) configuration and the double bond in the 3-side chain may have E or Z structure useful in combatting pests such as insects, nematodes acarids.

26 Claims, No Drawings

2-FLUORO-2-CYANOETHENYL CYCLOPROPANE CARBOXYLATES AS PESTICIDES

STATE OF THE ART

British Patent Application No. 2,099,810 describes insecticidal compounds of the formula

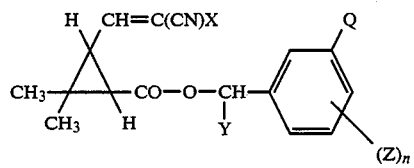

wherein X is a fluorine, chlorine or bromine atom, Y is hydrogen, cyano or ethynyl, and Z is a halogen atom, n is 0 to 4 and Q is hydrogen, halogen or phenoxy; methods for their manufacture; pesticidal compositions containing them and their use as pesticides, e.g. insecticides.

OBJECTS OF THE INVENTION

It is an object of the invention to provide the novel compounds of formula I and a process for their preparation.

It is another object of the invention to provide novel pesticidal compositions and a novel method of killing pests.

These and other objects and advantages of the invention will become obvious from the following detailed description.

THE INVENTION

The novel compounds of the invention are cyclopropanecarboxylates in all possible isomeric forms or mixtures thereof of the formula

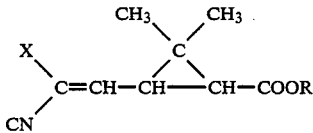

with a 1R,cis or 1R,trans structure and wherein X is a halogen, R is selected from the group consisting of (A) optionally unsaturated alkyl of 2 to 12 carbon atoms, (B) optionally unsaturated cycloalkyl of 3 to 12 carbon atoms, (c)

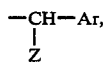

Z is selected from the group consisting of —C≡CH, —CH$_3$ and —CN and Ar is selected from the group consisting of —C$_6$H$_5$, —C$_6$F$_5$,

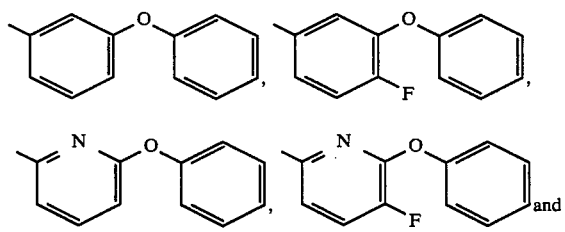

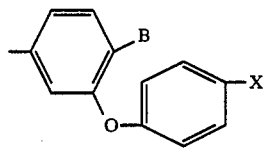

B is hydrogen or fluorine and X is fluorine, chlorine or bromine

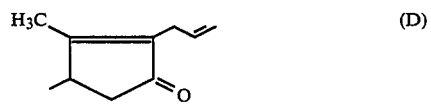

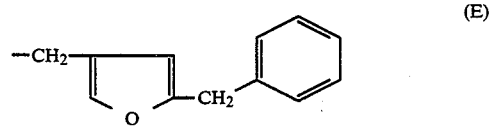

and

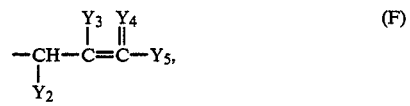

Y$_2$ is selected from the group consisting of hydrogen, fluorine, chlorine, bromine, —C≡N and —C≡CH, Y$_3$, Y$_4$, and Y$_5$ are individually selected from the group consisting of hydrogen, fluorine, chlorine, bromine atom, alkyl of 1 to 8 carbon atoms and cycloalkyl of 3 to 8 carbon atoms optionally substituted by one or more functional groups, alkenyl of 2 to 8 carbon atoms and alkynyl of 2 to 8 carbon atoms, and two of Y$_3$, Y$_4$ and Y$_5$ can form rings between them with the proviso that if X is bromine and R is

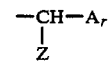

and Z is cyano or ethynyl and A$_r$ is

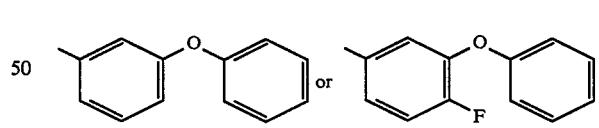

the carbon carrying Z is in the (S) configuration and the double bond in the 3-side chain may have E or Z structure.

Examples of R are optionally unsaturated alkyl such as ethyl, propyl, isopropyl and linear or branched butyl, pentyl and hexyl, 1-propenyl, 1-butynyl, 1,3-butadienyl and 1-pentenyl and optionally unsaturated cycloalkyl such as cyclopropyl, cyclobutyl, cyclopentyl, cyclohexyl, 1-cyclobutynyl, 1-cyclopentadienyl and 1-cyclohexenyl. The halogens include fluorine, chlorine and bromine and X is preferably fluorine.

Among the preferred compounds of formula I are those wherein the double bond in the 3-side chain has the Z structure and those wherein R is

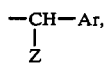

Z is —C≡CH, —CH₃ or —CN and Ar is selected from the group consisting of —C₆H₅, —C₆F₅,

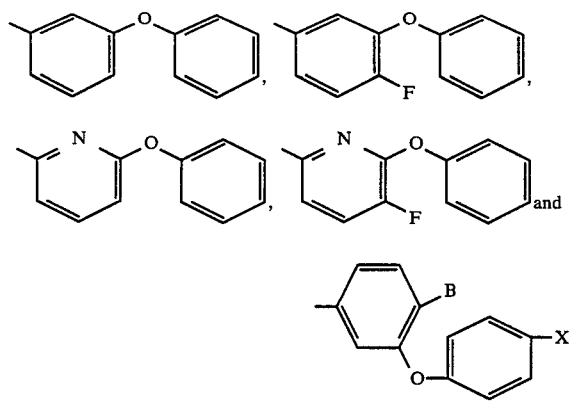

B is hydrogen or fluorine and X is fluorine, chlorine or bromine. Most preferably, Ar is α-cyano-3-phenoxybenzyl.

Other preferred compounds of formula I are those wherein X is bromine and R is

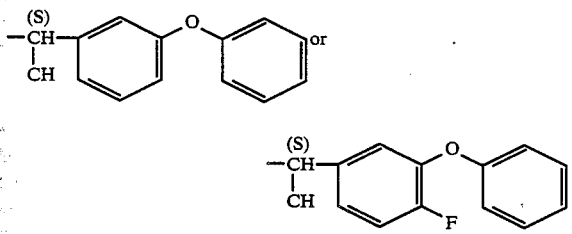

and the cyclopropane ring is of 1R cis configuration and those wherein X is chlorine or fluorine, R is

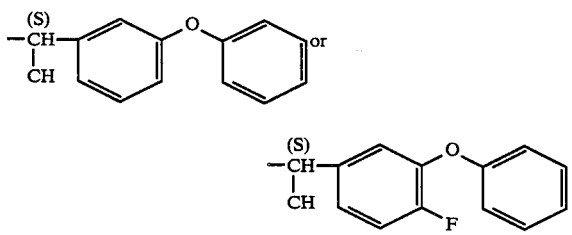

and the cyclopropane ring is in the 1R cis configuration.

Specific preferred compounds of formula I are (S) α-cyano-3-phenoxybenzyl 1R cis 2,2-dimethyl-3-[ΔE-2-fluoro-2-cyanoethenyl]cyclopropanecarboxylate and the corresponding Z isomer; (S) α-cyano-3-phenoxybenzyl 1R cis 2,2-dimethyl-3-[ΔE-2-bromo-2-cyanoethenyl]cyclopropane carboxylate and the corresponding ΔZ isomer; (S) α-cyano-3-phenoxy-4-fluoro-benzyl 1R cis 2,2-dimethyl-3-[ΔE-2-bromo-2-cyanoethenyl]cyclopropane carboxylate and the corresponding ΔZ isomer; (S) α-cyano-3-phenoxy-4-fluoro-benzyl 1R cis 2,2-dimethyl-3-[ΔE-2-fluoro-2-cyanoethenyl]cyclopropane carboxylate and the corresponding ΔZ isomer; (R,S) cyano-2-(6-phenoxypyridyl)-methyl 1R cis 2,2-dimethyl-3-[ΔE-2-fluoro-2-cyanoethenyl]cyclopropane carboxylate and the corresponding ΔZ isomer.

The novel process of the invention for the preparation of the compounds of formula I comprises subjecting a compound of the formula

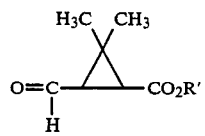

wherein R' is hydrogen atom or R of the above definition to the Wittig reaction with a compound of the formula

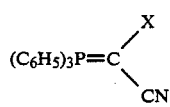

wherein X has the above definition to obtain a corresponding compound of formula I which is reacted with an esterification agent if R' is hydrogen, or which if desired, is subjected to the action of a cleavage agent for the ester function and then reacted with an esterification agent.

The compounds of formulae II, III are known products. When R is hydrogen and the configuration is cis, the compounds of formula II can be present in the lactone form. The products of formula III can be prepared by the process described in *Helv. Chem. Acta.* Vol. 60 (1977) p. 585.

The Wittig reaction used to prepare products of formula I provides compounds of formula I in which the geometry is E+Z. The isomers relative to the double bond can be separated, if desired, by physical methods such as chromatography whether relating to the acids or to the alkyl esters, or to other esters.

The cleavage agent for the —CO₂R is preferably heat used with an acid hydrolysis agent such as p-toluene sulfonic acid. The esterification can be carried out, in the presence of a tertiary base such as pyridine and preferably in the presence of a mixture of dicyclohexylcarbodiimide and 4-dimethyl aminopyridine or pyridine. The Wittig reaction, cleavage of ester functions, and esterification are reactions well-known to specialists and do not have to be detailed here.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

The insecticidal compositions of the invention are particularly preferred and may contain 0.005 to 10% by weight of the active ingredient. Among the preferred notable insecticidal compositions of the invention are those wherein the active compound is selected from the group consisting of (S) α-cyano-3-phenoxybenzyl 1R cis 2,2-dimethyl-3-[ΔE-2-fluoro-2-cyanoethenyl]cyclopropane carboxylate and the corresponding ΔZ isomer; (S) α-cyano-3-phenoxybenzyl 1R cis 2,2-dimethyl-3-[ΔE-2-bromo-2-cyanoethenyl]cyclopropane carboxylate and the corresponding ΔZ isomer; (S) α-cyano-3-phenoxy-4-fluorobenzyl 1R cis 2,2-dimethyl-3-[ΔE-2-bromo-2-cyanoethenyl]cyclopropane carboxylate and the corresponding ΔZ isomer; (S) α-cyano-3-phenoxy-4-fluorobenzyl 1R cis 2,2-dimethyl-3-[ΔE-2-fluoro-2-cyanoethenyl]cyclopropane carboxylate and the corresponding ΔZ isomer; (R,S) cyano-2-(6-phenoxy pyridyl)-methyl 1R cis 2,2-dimethyl-3-[ΔE-2-fluoro-2-cyanoethenyl]cyclopropane carboxylate and the corresponding ΔZ isomer.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 25% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premise use may be prepared as a spraying oil containing the active ingredient and the oil may soak the wick of a lamp which is then subjected to combustion. The concentration of the compound of formula I in the oil is preferably 0.03 to 25% by weight.

The compositions of the invention are also useful to combat acariens and nematode parasites of vegetables containing at least one compound of formula I as the active ingredient and they may be in the form of powders, granules, suspensions, emulsions or solutions.

For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

The compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid.

The compositions of the invention are also useful to combat acarien parasites of warm-blooded animals such as ticks, especially ticks of Boophilus species, Hyalomnia species, Amblyomnia species and Rhipicephalus species and to combat all sorts of scabies such as sarcoptic scabies, psoroptic scabies and chorioptic scabies. They can also be useful to combat lice and helminthes. The invention also includes compositions intended to combat parasites of warm-blooded animals, especially ticks and gales, containing at least one compound of formula I.

The said compounds may be administered externally by vaporization, by painting or by bathing. For veterinary usage, the compositions may also be administered by painting the dorsal spine by the "pour on" method. When the "pour on" method is used it is preferred to use solutions containing from 0.5 to 4 g of active material per 100 $cm^3$ of solution.

When the compositions are to be used to combat parasitic acariens of animals, the active compounds of formula I are very often incorporated into alimentary compositions in association with a nutritive mixture adapted to the animal to be fed. The nutritive mixture will vary depending upon the species of animal but usually contains cereals, sugars and grains, soybean press cake, peanuts and turnsole press cakes, meal of animal origin such as fish meal, synthetic amino acids, mineral salts, vitamins and antioxidants.

Another feature of the invention are insecticidal, aracicidal or nematocidal compositions containing as an active ingredient at least one compound of formula I and as a second active ingredient at least one pyrethrinoid ester selected from the group consisting of esters of allethrolone, of 3,4,5,6-tetrahydrophthalimidomethyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furylmethyl alcohol with 2,2-dimethyl-3-(2-oxo-3-tetrahydrothiophenylidene methyl)-cyclopropane-1-carboxylic acids, esters of 3-phenoxybenzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimidomethyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

To increase the biological activity of the compositions of the invention, classical synergists may be incorporated therein such as 1-(2,5,8-trioxadodecyl)-2-propyl-4,5-methylenedioxybenzene (piperonyl butoxide) or N-(2-ethyl-heptyl)-bicyclo-[2,2.1]-5-heptene-2,3-dicarboximide or piperonyl-bis-2-(2'-n-butoxyethoxy)-ethyl acetal (tropital).

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

(1R cis) 2,2-dimethyl-3-[(E+Z)-2-bromo-2-cyanoethenyl]-cyclopropane carboxylic acid Under an inert atmosphere, a solution of 3.5 g of bromocyanomethylene-triphenylphosphorane, 30 ml of tetrahydrofuran and 4 ml of dimethylformamide was formed and a solution of 1.3 g of (1R cis) 2,2-dimethyl-dihydroxymethyl-cyclopropane carboxylic acid lactone and 10 ml of tetrahydrofuran were added thereto. The mixture was held for 16 hours at room temperature and was evaporated to dryness to obtain 5.8 g of an oily residue which was chromatographed over silica gel. Elution with a hexane-ethyl acetate (7/3) mixture with 1% of acetic acid yielded (1R cis) 2,2-dimethyl-3-[(E+Z)-2-bromo-2-cyanoethenyl]-cyclopropane carboxylic acid melting at 132° C.

EXAMPLE 2

(S) α-cyano-3-phenoxy-benzyl (1R cis) 2,2-dimethyl-3-[(ΔE)-2-bromo-2-cyanoethenyl]-cyclopropane carboxylate and corresponding ΔZ isomer 30 mg of 4 dimethylaminopyridine were added at 0° to +5° C. to 10 ml of a solution containing 1.4 g (1R cis) 2,2-dimethyl-3-[(E+Z)-2-bromo-2-cyanoethenyl]-cyclopropane carboxylic acid and 1.4 g of (S) α-cyano-3-phenoxybenzyl alcohol, and then 1.2 g of dicyclohexylcarbodiimide and 5 ml of methylene chloride were added thereto. The mixture was allowed to return to 10° C. and was stirred for 3 hours and the urea formed was filtered off. The filtrate was rinsed and evaporated to dryness to obtain 3.7 g of (S) α-cyano-3-phenoxy-benzyl (1R cis) 2,2-dimethyl-3-[(ΔE)-2-bromo-2-cyanoethenyl]-cyclopropane carboxylate and corresponding Z isomer which was chromatographed over silica gel. Elution with benzene yielded 1,3 g of ΔE isomer melting at 60° C. and 750 mg of ΔZ of isomer melting at 64° C.

EXAMPLE 3

Tert.-butyl (1R cis) 2,2-dimethyl-3-[(ΔZ)-2-fluoro-2-cyanoethenyl]-cyclopropane carboxylate and the corresponding ΔE isomer 15 g of phenyl bromofluorocyanomethyl mercury, 180 ml of xylene, 8 g of triphenylphosphine and 5.25 g of tert.-butyl (1R cis) 2,2-dimethyl-3-formyl-cyclopropane-1-carboxylate were refluxed with stirring for 1 hour and was then cooled and filtered. The filtrate was evaporated to dryness to obtain 20 g of (1R cis) tert.-butyl 2,2-dimethyl-3-[(ΔZ)-2-fluoro-2-cyanoethenyl]-cyclopropane carboxylate and the corresponding ΔE isomer residue which was chromatographed over silica gel. Elution with pure benzene yielded 3 g of ΔE isomer with an Rf=0.4 and 1.3 g of ΔZ isomer with an Rf=0.33.

Preparation of phenyl bromofluorocyanomethyl mercury

STEP A: Bromofluoro acetamide

At +5° C., 86 ml of concentrated ammonium hydroxide were added to 79 g of ethyl bromofluoroacetate with strong stirring and the temperature and the stirring were maintained for another 30 minutes. Then, after evaporation to dryness, the residue was distilled to obtain 53.6 g of bromofluoro acetamide with a boiling point of 82°–84° C. at 0.1 mm Hg.

STEP B: Bromofluoro acetonitrile 92 g of phosphoric anhydride were added to 183 g of bromofluoro acetamide of Step A and the mixture was heated progressively to 200° C. (exterior) to obtain 87 g of the crude bromofluoro acetonitrile distilling off between 55° C. and 80° C.

STEP C: Phenyl bromofluorocyanomethyl mercury 15.65 g of phenyl mercuric chloride in 100 ml of tetrahydrofuran were cooled to −50° C. and 10.6 g of fluorobromo acetonitrile of Step B were added. Then, still at −50° C. a suspension of 7.85 g of potassium tert-butylate, 50 ml of tetrahydrofuran and 6.6 ml of tert.-butyl alcohol was added thereto with stirring. After 30 minutes, the mixture was poured into iced water containing 6 ml of concentrated hydrochloric acid, and the mixture was extracted with chloroform. The organic phase was dried and evaporated to dryness. The residue was taken up in a chloroformhexane (1/1) mixture and the insoluble matter was filtered off. The mixture was cooled and filtered to obtain 9.3 g of phenyl bromofluorocyanomethyl mercury melting at 130°–132° C.

EXAMPLE 4

(1R cis) 2,2-dimethyl-3-[(ΔZ)-2-cyano-2-fluoroethenyl]cyclopropane carboxylic acid A mixture of 1.3 g of tert.-butyl (1R cis) 2,2-dimethyl-3-[(ΔZ)-2-cyano-2-fluoroethenyl]-cyclopropane carboxylate. 13 ml of methyl-benzene and 130 ml of p-toluenesulfonic acid was heated to 120°–130° C. and the mixture was stirred for 15 minutes after reflux commenced. The mixture was cooled to 20° C. and was washed with water. The toluene solution was dried over sodium sulfate, filtered and evaporated to dryness under reduced pressure to obtain 1 g of (1R cis) 2,2-dimethyl-3-[(ΔZ)-2-cyano-2-fluoroethenyl]-cyclopropane carboxylic acid.

EXAMPLE 5

(1R cis) 2,2-dimethyl-3-[(ΔE)-2-cyano-2-fluoroethenyl]-cyclopropane carboxylic acid Using the procedure of Example 4, tert-butyl (1R cis) 2,2-dimethyl-3-[(ΔE)-2-fluloro-2-cyanoethenyl]cyclopropane carboxylate was reacted to obtain (1R cis) 2,2-dimethyl-3-[(ΔE)-2-cyano-2-fluoroethenyl]-cyclopropane carboxylic acid.

EXAMPLE 6

(S) α-cyano-3-phenoxy-benzyl (1R cis) 2,2-dimethyl-3-[(ΔZ)-2-fluoro-2-cyanoethenyl]-cyclopropane carboxylate 30 g of 4-dimethylamino-pyridine were added at 5° C. to a solution of 1 g of (1R cis) 2,2-dimethyl-3-[(ΔZ)-2-fluoro-2-cyanoethenyl]-cyclopropane carboxylic acid, 6 ml of methylene chloride and 1.2 g of (S) α-cyano-3-phenoxybenzyl alcohol and then 1.1 g of dicyclohexylcarbodiimide and 8 ml of methylene chloride were added. The mixture was allowed to return to 20° C. and was stirred for 2 hours. 0.5 ml of acetic acid and 0.5 ml of ethanol were then added and the urea formed was filtered off. The filter was rinsed with a little methylene chloride and the filtrate was evaporated to dryness to obtain 2.8 g of residue which was chromatographed over silica gel. Elution with a methylene chloride-hexane (8/2) mixture yielded 1.5 g of the product which was crystallized from refluxing isopropanol to obtain 1.3 g of (S) α-cyano-3-phenoxy-benzyl (1R cis) 2,2-dimethyl-3-[(ΔZ)-2-fluoro-2-cyanoethenyl]-cyclopropane carboxylate melting at 90° C.

EXAMPLE 7

(1R cis) 2,2-dimethyl-3-[(E+Z)-2-chloro-2-cyanoethenyl]cyclopropane carboxylic acid Using the procedure of Example 1, chlorocyanomethyltriphenyl phosphorane was reacted to obtain (1R cis) 2,2-dimethyl-3-[(E+Z)-2-chloro-2-cyanoethenyl]-cyclopropane carboxylic acid melting at <50° C.

EXAMPLE 8

(S) α-cyano-3-phenoxy-benzyl (1R cis) 2,2-dimethyl-3-[(ΔE)-2-chloro-2-cyanoethenyl]-cyclopropane carboxylate and the corresponding ΔZ isomer Using the procedure of Example 2, the acid of Example 7 was reacted to obtain the ΔE isomer melting at 66° C. and the ΔZ isomer melting at 63° C.

EXAMPLE 9

(S) α-cyano-3-phenoxy-benzyl (1R trans) 2,2-dimethyl-3-[(ΔE)-2-cyano-2-fluoroethenyl]-cyclopropane carboxylate and the corresponding ΔZ isomer A mixture of 10 g of (S) α-cyano-3-phenoxybenzyl (1R trans) 2,2-dimethyl-3-formyl-cyclopropane carboxylate, 8 g of triphenylphosphine, 180 ml of xylene and 15 g of phenyl bromocyanofluoromethyl mercury was refluxed with stirring for 2 hours and was then cooled and filtered. The filtrate was evaporated to dryness to obtain 24 g of an oil residue which was chromatographed over silica gel. Elution with toluene. After repeating the high performance layer chromatography several times, there was obtained 835 mg of ΔZ isomer with a specific rotation of $[\alpha]_D = 17° \pm 1.5°$ (c=1% in CHCl$_3$) and 1.8 g of ΔE isomer with a specific rotation of $[\alpha]_D = -21° \pm 2.5°$ (c=0.5% in CHCl$_3$).

EXAMPLES 10 to 24

Using the procedures, compounds of formula I were obtained as reported in the following Table.

| Example | X | Δ | Geometry | R | |
|---|---|---|---|---|---|
| 10 | F | E | 1Rcis | —CH(CN)—C$_6$H$_4$—O—C$_6$H$_5$ | $\alpha_D = +57°5 \pm 3°$(c = 0,4% CHCl$_3$) |
| 11 | Br | E | 1Rcis | —CH(CN)—C$_6$H$_3$(F)—O—C$_6$H$_5$ | $\alpha_D = +50°5 \pm 1°5$(c = 1% toluene) |
|  | Br | Z | 1Rcis |  | $\alpha_D = +65° \pm 2°5$(c = 0,5% toluene) |
| 12 | Br | E | 1Rcis | (N,N'-propargyl hydantoinyl-CH$_2$) | F = 147° C. (ΔE) |
|  | Br | Z | 1Rcis |  | $\alpha_D = 6° + 2°$(c = 0,7% toluene (ΔZ)) |
| 13 | Br | E | 1Rcis | (S)-methyl-allyl-cyclopentenone | $\alpha_D = +41°5 \pm 2°5$(c = 0,5% toluene) |
| 14 | Br | E | 1Rcis | —CH(CN)—(2-phenyl-pyridin-6-yl) | $\alpha_D = -6°$(c = 0,3% toluene) |

-continued

| Example | X | Δ | Geometry | | R |
|---------|---|---|----------|---|---|
| 15 | Cl | Z on E | 1Rtrans | 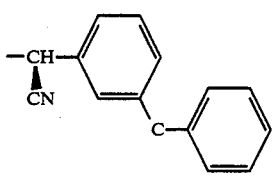 | $\alpha_D = +41° \pm 1°$ (c = 1% toluene) |
| 16 | Cl | E on Z | 1Rtrans | 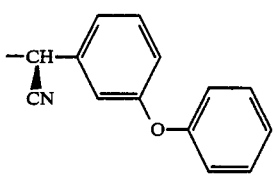 | F = 94° C. $\alpha_D = +77° \pm 2°$ (c = 1% toluene) |
| 17 | Cl<br>Cl | E<br>Z | 1Rcis<br>1Rcis | 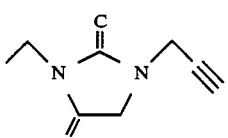 | $\alpha_D = -35° \pm 2°5$ (c = 0,5% CHCl$_3$)<br>$\alpha_D = -9°5 \pm 2°$ (c = 0,5% CHCl$_3$) |
| 18 | Cl<br>Cl | E<br>Z | 1Rcis<br>1Rcis | 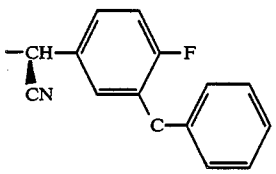 | $\alpha_D = +24° \pm 2°5$ (c = 0,5% CHCl$_3$)<br>$\alpha_D = +38° \pm 2°5$ (c = 0,5% CHCl$_3$) |
| 19 | Cl | E + Z | 1Rcis | 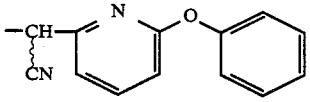 | $\alpha_D = +5°$ (c = 0,5% CHCl$_3$) |
| 20 | Cl<br>Cl | E<br>Z | 1Rtrans<br>1Rtrans | 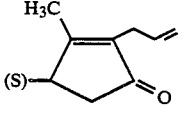 | $\alpha_D = +56° \pm 3°5$ (c = 0,35% CHCl$_3$)<br>$\alpha_D = +17° \pm 2°5$ (c = 0,5% CHCl$_3$) |
| 21 | F | F | 1Rcis | 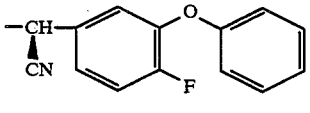 | $\alpha_D = +86° \pm 4°$ (c = 0,2% CHCl$_3$) |
| 22 | F | E | 1Rcis | 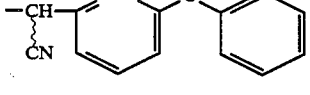 | $\alpha_D = +61° \pm 4°$ (c = 0,2% CHCl$_3$) |
| 23 | F | Z | 1Rcis | 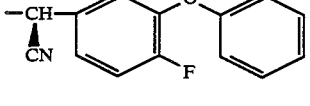 | F = +124° C. |
| 24 | F | Z | 1Rcis | 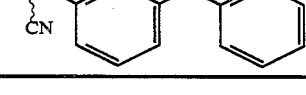 | $\alpha_D = -31°5 \pm 4°$ (c = 0,2% CHCl$_3$) |

That is to say:

10. (S) α-cyano-3-phenoxybenzyl (1R cis) 2,2-dimethyl-3-[(ΔE)-2-fluoro-2-cyanoethenyl]-cyclopropane carboxylate;

11. (S) α-cyano-4-fluoro-3-phenoxybenzyl (1R cis) 2,2-dimethyl-3-[(ΔE)-2-bromo-2-cyanoethenyl]-cyclopropane carboxylate and the (ΔZ) isomer;

12. (3-propyn-2-yl-2,5-dioxo-imidazolidinyl)-methyl (1R cis) 2,2-dimethyl-3-[(ΔE)-2-bromo-2-cyanoethenyl]-cyclopropane carboxylate and the (ΔZ) isomer;
13. (1S)-2-methyl-4-oxo-3-(2-propenyl)-2-cyclopenten-1-yl (1R cis) 2,2-dimethyl-3-[(ΔE)-2-bromo-2-cyanoethenyl]-cyclopropane carboxylate;
14. (R,S) cyano-2-(6-phenoxypyridyl)-methyl (1R cis) 2,2-dimethyl-3-[(ΔE)-2-bromo-2-cyanoethenyl]-cyclopropane carboxylate;
15-16.(S) α-cyano-3-phenoxybenzyl (1R trans) 2,2-dimethyl-3-[(ΔE)-2-chloro-2-cyanoethenyl]-cyclopropane carboxylate and the (ΔZ) isomer;
17. (3-propyn-2-yl-2,5-dioxo imidazolidinyl)-methyl (1R cis) 2,2-dimethyl-3-[(ΔE)-2-chloro-2-cyanoethenyl]-cyclopropane carboxylate and the (ΔZ) isomer;
18. (S) α-cyano-3-phenoxy-4-fluorobenzyl (1R cis) 2,2-dimethyl-3-[(ΔE)-2-chloro-2-cyanoethenyl]-cyclopropane carboxylate and the (ΔZ) isomer;
19. (R,S) cyano-2-(6-phenoxypyridyl)-methyl (1R cis) 2,2-dimethyl-3-[(ΔE+ΔZ)-2-chloro-2-cyanoethenyl]-cyclopropane carboxylate;
20. (1S)-2-methyl-4-oxo-3-(2-propenyl)-2-cyclopenten-1-yl (1R cis) 2,2-dimethyl-3-[(ΔE)-2-chloro-2-cyanoethenyl]-cyclopropane carboxylate;
21. (S) α-cyano-3-phenoxy-4-fluorobenzyl (1R cis) 2,2-dimethyl-3-[(ΔE)-2-fluoro-2-cyanoethenyl]-cyclopropane carboxylate;
22. (R,S) cyano-2-(6-phenoxypyridyl)-methyl (1R cis) 2,2-dimethyl-3-[(ΔE)-2-fluoro-2-cyanoethenyl]-cyclopropane carboxylate;
23. (S) α-cyano-3-phenoxy-4-fluorobenzyl (1R, cis) 2,2-dimethyl-3-[(ΔZ)-2-fluoro-2-cyanoethenyl]-cyclopropane carboxylate;
24. (R,S) cyano-2-(6-phenoxypyridyl)-methyl (1R cis) 2,2-dimethyl-3-[(ΔZ)-2-fluoro-2-cyanoethenyl]-cyclopropane carboxylate.

EXAMPLE 25

(1R cis) 2,2-dimethyl-3-[(ΔZ)-2-bromo-2-cyanoethenyl]-cyclopropane carboxylic acid

STEP A: Tert.-butyl (1R cis) 2,2-dimethyl-3-[(Z)-2-bromo-2-cyanoethenyl]-cyclopropane carboxylate and the (E) isomer 7.5 g of bromocyanomethylenetriphenyl phosphorane in 50 ml of tetrahydrofuran and 4 g of tert.-butyl (1R cis) 2,2-dimethyl-3-formyl-cyclopropane carboxylate in 50 ml of tetrahydrofuran were mixed together and the mixture was refluxed for 20 hours. After cooling and filtration, the filtrate was evaporated to dryness under reduced pressure and the residue was taken up in 100 ml of isopropyl ether. The soluble matter was filtered off and the filtrate was evaporated to dryness. The residue was chromatographed over silica gel and elution with a hexane-ethyl acetate (95/5) mixture yielded 1.4 g of (E) isomer melting at 102°-103° C. and 0.4 g of (Z) isomer melting at <50° C. and 0.7 g of a mixture of (E) and (Z) isomers.

STEP B: (1R cis) 2,2-dimethyl-3-[(Z)-2-bromo-2-cyanoethenyl]-cyclopropane carboxylic acid 1.5 g of the (Z) isomer obtained in Step A, 50 ml of anhydrous toluene and 150 mg of p-toluene sulfonic acid were refluxed for 30 minutes and after cooling to room temperature, the organic phase was washed with water, dried and evaporated to dryness to obtain 1.2 g of (1R cis) 2,2-dimethyl-3-[(Z)-2-bromo-2-cyanoethenyl]cyclopropane carboylic acid melting at 139°-140° C.

EXAMPLE 26

(1R trans) 2,2-dimethyl-3-[(E+Z)-2-bromo-2-cyanoethenyl]-cyclopropane carboxylic acid

STEP A: Tert.-butyl (1R trans) 2,2-dimethyl-3-[(E+Z)-2-bromo-2-cyanoethenyl]-cyclopropane carboxylate Using the procedure of Step A of Example 25, 4 g of tert-butyl (1R trans 2,2-dimethyl-3-formyl-cyclopropane carboxylate were reacted to obtain 2.7 g of tert.-butyl (1R trans) 2,2-dimethyl-3-[(E+Z)-2-bromo-2-cyanoethenyl]-cyclopropane carboxylate melting at 88° C.

STEP B: (1R trans) 2,2-dimethyl-3-[(E+Z)-2-bromo-2-cyanoethenyl]-cyclopropane carboxylic acid Using the procedure of Step B of Example 25, 2.7 g of the product of Step A were reacted to obtain 2.05 g of (1R trans) 2,2-dimethyl-3-[(E+Z)-2-bromo-2-cyanoethenyl]cyclopropane carboxylic acid melting at 136° C. (not very clear).

EXAMPLE 27

(R,S)2-(6-phenoxypyridyl)-ethyl (1R cis) 2,2-dimethyl-3[(Z)-2-chloro-2-cyanoethenyl]-cyclopropane carboxylate and (R,S)2-(6-phenoxypyridyl-ethyl (1R cis) 2,2-dimethyl-3-[(E)-2-chloro-2-cyanoethenyl]-cyclopropane carboxylate Using the procedure of Example 25, (1R cis) 2,2-dimethyl-3-[(E+Z)-2-chloro-2-cyanoethenyl]-cyclopropane carboxylic acid was esterified with (R,S)2-(6-phenoxypyridyl)-ethyl alcohol and the ester obtained was chromatographed over silica gel. Elution with a mixture of hexane and ethyl acetate (8/2), then a mixture of hexane and ethyl acetate (7.5/2.5) yielded 1.08 g of (E) isomer and 2.65 g of a mixture which was again purified by chromatography over silica gel and elution with a hexane-ethyl acetate (9/1) mixture to obtain 1.20 g of (Z) isomer.

(E) Isomer: $[α]_D = 52.5°$ (c=0.5% chloroform).
(Z) Isomer: $[α]_D = +14.5°$ (c=0.5% chloroform).

EXAMPLE 28

(R,S)cyano-2-(6-phenoxypyridyl)-methyl (1R cis) 2,2-dimethyl-3-[(Z)-2-bromo-2-cyanoethenyl]-cyclopropane carboxylate Using the procedure of Example 26, (1R cis) 2,2-dimethyl-3-[(Z)-2-bromo-2-cyanoethenyl]-cyclopropane carboxylic acid of Example 25 and (R,S)cyano-2-(6-phenoxypyridyl)-methyl alcohol were reacted to obtain (R,S)cyano-2-(6-phenoxypyridyl)-methyl (1R cis) 2,2-dimethyl-3-[(Z)-2-bromo-2-cyanoethenyl]-cyclopropane carboxylate with a specific rotation of $[α]_D = +3°$ (c=1% in toluene).

EXAMPLE 29

(S)α-cyano-3-phenoxy-benzyl (1R trans) 2,2-dimethyl-3-[(E)-2-bromo-2-cyanoethenyl]-cyclopropane carboxylate and (S)α-cyano-3-phenoxy-benzyl (1R trans) 2,2-dimethyl-3-[(Z)-2-bromo-2-cyanoethenyl]-cyclopropane carboxylate Using the procedure of Example 27, the acid of Example 26 and the appropriate alcohol were reacted to obtain the (E) isomer melting at 118° C. and with a specific rotation of $[\alpha]_D = +20°$ (c=1.2% in chloroform) and the (Z) isomer melting at 115° C.

EXAMPLE 30

(S)2-methyl-4-oxo-3-(2-propenyl)-2-cyclopenten-1-yl (1R cis) 2,2-dimethyl-3-[(Z)-2-bromo-2-cyanoethenyl]-cyclopropane carboxylate Using the procedure of Example 27, the acid of Example 25 and the appropriate alcohol were reacted to obtain (S)2-methyl-4-oxo-3-(2-propenyl)-2-cyclopenten-1-yl (1R cis) 2,2-dimethyl-3-[(Z)-2-bromo-2-cyanoethenyl]-cyclopropane carboxylate.

NMR Spectrum (deuterochloroform): Peak at 1.3 ppm (hydrogens of geminal methyls); at 2.0 ppm (hydrogens of 2-methyl of allethrolone); at 4.8–5.25 ppm (hydrogens of methylene

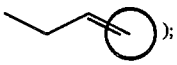

at 5.5–6.2 ppm (hydrogen of

at 5.7 ppm (1-hydrogen of allethrolone); and at 7.3–7.5 ppm (ethylene hydrogen of double bond carrying—CN and—Br).

EXAMPLE 31

Preparation of a soluble concentrate

A homogeneous mixture was made of 0.25 g of the product of Example 6, 1.00 g of piperonyl butoxide, 0.25 g of Tween 80, 0.1 g of Topanol A and 98.4 g of Water.

EXAMPLE 32

Preparation of an emulsifiable concentrate

A homogeneous mixture was formed of 0.015 g of the product of Example 10, 0.5 g of piperonyl butoxide, 0.1 g of Topanol A, 3.5 g of Tween 80 and 95.885 g of Xylene.

EXAMPLE 33

Preparation of a soluble concentrate

A homogeneous mixture was prepared from 0.25 g of the product of Example 19, 1 g of piperonyl butoxide, 0.25 g of Tween 80, 0.1 g of Topanol A and 98.4 g of Water.

EXAMPLE 34

Preparation of an emulsifiable concentrate

The following were mixed intimately: 0.015 g of the product of Example 27 (Z isomer), 0.5 g of piperonyl butoxide, 0.1 g of Topanol A, 3.5 g of Tween 80 and 95.885 g of Xylene.

EXAMPLE 35

Preparation of an emulsifiable concentrate

A homogeneous mixture was prepared containing 1.5 g of the product of Example 27 (E isomer), 20. g of Tween 80, 0.1 g of Topanol A and 78.4 g of Xylene.

EXAMPLE 36

Preparation of a fumigating composition

The following are mixed homogeneously; 0.25 g of the product of Example 28 (Z isomer), 25 g of tabu powder, 40 g of cedar leaf powder, 33.75 g of pine wood powder, 0.5 g of brilliant green and 0.5 g of p-nitrophenol.

PESTICIDAL DATA (A) Known down effect on house flies 4-day old female house flies, were subjected to direct atomization at a concentration of 0.25 g/l in a Kearns and March chamber using a mixture of acetone (5%) and Isopar L (petrol solvent) as solvent with the amount of solvent utilized being 2 ml in one second. 50 insects were used per treatment and checks were made every minute for 10 minutes and then at 15 minutes. The KT 50 was determined by the usual method and is reported in the following Table.

| COMPOUND OF EXAMPLE | KT 50 in minutes |
|---|---|
| 2 | 4.3 |
| 6 | 3.6 |
| 8 | 2.8 |
| 19 | 2.3 |
| 27 (E isomer) | 2.7 |
| 27 (Z isomer) | 3.3 |
| 28 (Z isomer) | 2.2 |
| 29 (E isomer) | 4.1 |
| 29 (Z isomer) | 4.8 |
| 14 | 2.7 |
| 21 | 1.9 |
| 22 | 1.4 |
| 23 | 3.0 |
| 24 | 1.9 |

(B) Lethal effect on cockroaches

The tests were carried out by contact on a film on glass formed by depositing different concentrations of acetone solutions with a pipette on the bottom of a glass Petri dish, the edges of which had previously been talced to prevent the escape of the insects. The 50% lethal concentration (LC 50), i.e., the dose which killed half the cockroaches was determined.

| COMPOUND OF EXAMPLE | LC 50 in mg/m² |
|---|---|
| 19 | 1.3 |
| 27 (E isomer) | 1.05 |
| 27 (Z isomer) | 1.07 |
| 28 (Z isomer) | 2.0 |
| 21 | 0.47 |

| COMPOUND OF EXAMPLE | LC 50 in mg/m² |
| --- | --- |
| 23 | 0.26 |

(C) Lethal Effect on Spodoptera littoralis larvae

The tests were carried out by topical application of a toxic acetone solution with an Arnold micromanipulator on the dorsal thorax of the caterpillars and the LD$_{50}$ was determined on 15 larvae per dose of the product under test. The caterpillars used were larvae of the fourth larval stage, that is to say, aged about 10 days and reared on an artificial medium (Poitout's medium) at 24° C. and 65% relative humidity. After treatment, the individuals were put under observation on an artificial nutritive medium and mortality checks were made 48 hours after treatment. The experimental results obtained for the products of Examples 2, 6, 8, 21 and 23 were between 0.48 and 4.8 ng per insect.

(D) Acaricidal effect

Bean plants comprising 2 leaves infested with 25 Tetranychus urticae females per leaf were placed under a ventilated hood under a luminous ceiling in constant light. The plants were treated with a Fisher gun using 4 ml per plant of the solution under test containing the pyrethrinoid in a mixture of equal volumes of water and acetone. This is allowed to dry for 12 hours before infestation and mortality checks were made after 80 hours. The LC 50 in mg/hl, i.e., the concentration for which 50% mortality is obtained, was determined and the results are summarized in the following Table:

| COMPOUND OF EXAMPLE | LC 50 mg/hl |
| --- | --- |
| 27 (E isomer) | 2303 |
| 27 (Z isomer) | 3420 |

CONCLUSION

The invention compounds are endowed with a good biological activity against the parasites tested.

Various modifications of the compounds and methods of the invention may be made without departing from the spirit or scope thereof and it is to be understood that the invention is intended to be limited only as defined in the appended claims.

What we claim is:

1. A cyclopropanecarboxylate in all possible isomeric forms or mixtures thereof of the formula

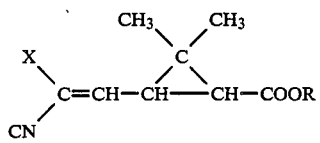

with a 1R,cis, (E) or (Z) structure and wherein X is fluorine, R is selected from the group consisting of (A) optionally unsaturated alkyl of 2 to 12 carbon atoms, (B) optionally unsaturated cycloalkyl of 3 to 12 carbon atoms, (c)

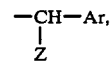

Z is selected from the group consisting of —C≡CH, —CH$_3$ and —CN and Ar is selected from the group consisting of —C$_6$H$_5$, —C$_6$F$_5$,

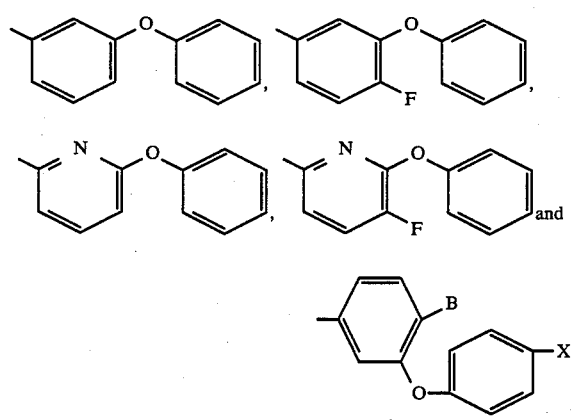

B is hydrogen or fluorine and X is fluorine, chlorine or bromine

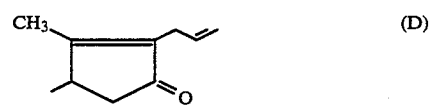

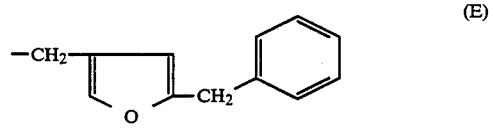

and

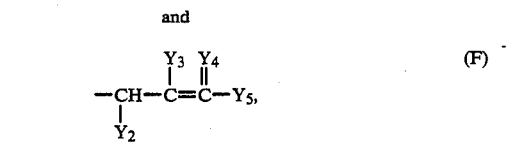

Y$_2$ is selected from the group consisting of hydrogen, fluorine, chlorine, bromine, —C≡N and —C≡CH, Y$_3$, Y$_4$ and Y$_5$ are individually selected from the group consisting of hydrogen, fluorine, chlorine, bromine alkyl of 1 to 8 carbon atoms and cycloalkyl of 3 to 8 carbon atoms alkenyl of 2 to 8 carbon atoms and alkynyl of 2 to 8 carbon atoms, and two of Y$_3$, Y$_4$ and Y$_5$ can form rings between them with the proviso that if X is bromine and R is

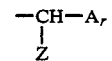

and Z is cyano or ethynyl and A$_r$ is

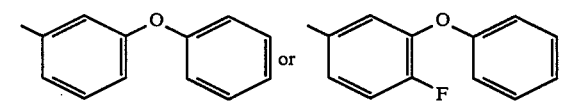

the carbon carrying Z is in the (S) configuration and the double bond in the 3-side chain may have E or Z structure.

2. A compound of claim 1 wherein the double bond in the 3-side chain has the Z structure.

3. A compound of claim 1 wherein R is

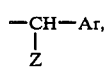

Z is —C≡CH, —CH₃, or —CN and Ar is selected from the group consisting of —C₆H₅, —C₆F₅,

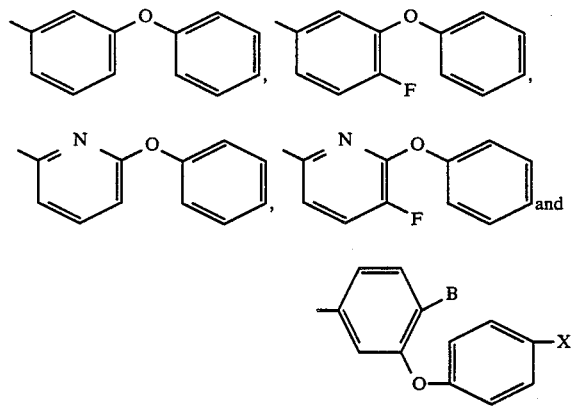

and B is hydrogen or fluorine.

4. A compound of claim 3 wherein Ar is α-cyano-3-phenoxy-benzyl.

5. A compound of claim 1 wherein R is

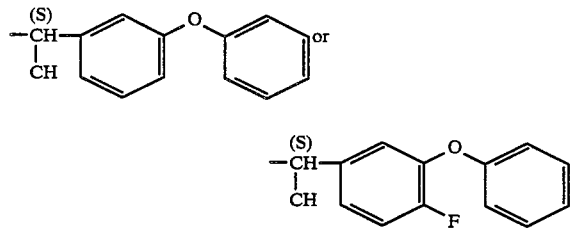

and the cyclopropane ring is in the 1R cis configuration.

6. A compound of claim 1 selected from the group consisting of (S)α-cyano-3-phenoxybenzyl 1R cis 2,2-dimethyl-3-[ΔE-2-fluoro-2-cyanoethenyl]cyclopropane carboxylate and the corresponding ΔZ isomer; (S)α-cyano-3-phenoxy-4-fluoro-benzyl 1R cis 2,2-dimethyl-3-[ΔE-2-fluoro-2-cyanoethenyl]cyclopropane carboxylate and the corresponding ΔZ isomer; (R,S)cyano-2-(6-phenoxypyridyl)-methyl 1R cis 2,2-dimethyl-3-[ΔE-2-fluoro-2-cyanoethenyl]cyclopropane carboxylate and the corresponding ΔZ isomer.

7. A pesticidal composition comprising an amount effective to combat insects, nematodes and parasitic acariens of at least one compound of claim 1 and an inert carrier.

8. A composition of claim 7 wherein the double bond in the 3-side chain has the Z structure.

9. A composition of claim 7 wherein R is —CH—Ar, Z is —C≡CH, —CH, or —CN and Ar is selected from the group consisting of —C₆H₅, —C₆H₅,

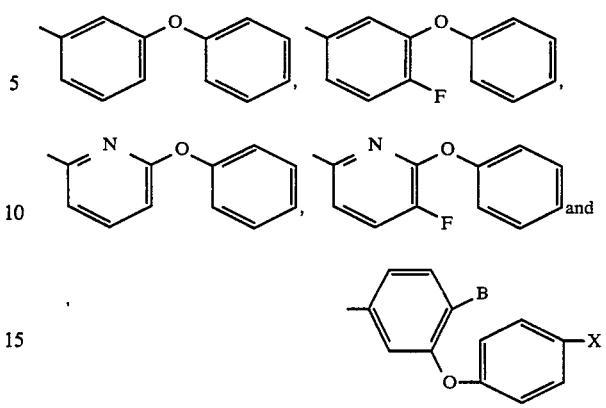

and B is hydrogen or fluorine.

10. A composition of claim 9 wherein Ar is α-cyano-3-phenoxy-benzyl.

11. A composition of claim 7 wherein R is

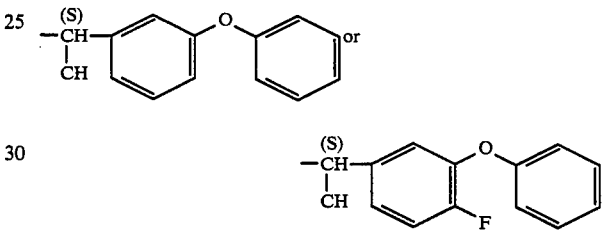

and the cyclopropane ring is in the 1R cis configuration.

12. A composition of claim 7 wherein the active compound is selected from the beginning consisting of (S)α-cyano-3-phenoxybenzyl 1R cis 2,2-dimethyl-3-[ΔE-2-fluoro-2-cyanoethenyl]cyclopropane carboxylate and the corresponding ΔZ isomer; (S)α-cyano-3-phenoxy-4-fluoro-benzyl 1R cis 2,2-dimethyl-3-[ΔE-2-fluoro-2-cyanoethenyl]cyclopropane carboxylate and the corresponding ΔZ isomer; (R,S) cyano-2-(6-phenoxypyridyl)-methyl 1R cis 2,2-dimethyl-3-[ΔE-2-fluoro-2-cyanoethenyl]cyclopropane carboxylate and the corresponding ΔZ isomer.

13. An insecticidal composition comprising an insecticidally effective amount of at least one compound of claim 1 and an inert carrier.

14. A nematocidal composition comprising a nematocidally effective amount of at least one compound of claim 1 and an inert carrier.

15. An acaricidal composition comprising an acaricidally effective amount of at least one compound of claim 1 and an inert carrier.

16. A composition for combatting affections caused by acariens in warm-blooded animals, comprising an anti-acarienly effective amount of at least one compound of claim 1 and an inert carrier.

17. A method of combatting pests selected from the group consisting of insects, nematodes and parasitic acariens comprising contacting pests with a pesticidally effective amount of at least one compound of claim 1.

18. A method of claim 17 wherein the double bond in the 3-side chain has the Z structure.

19. A method of claim 17 wherein R is —CH—Ar, Z is —C≡Ch, —CH, or —CN and Ar is selected from the group consisting of —C₆H₅, —C₆F₅,

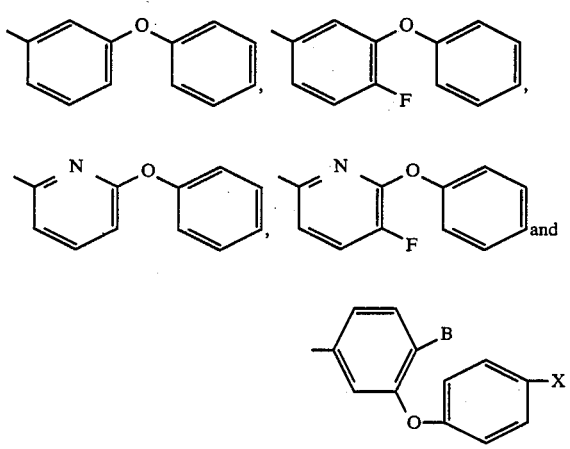

and B is hydrogen or fluorine.

20. A method of claim 17 wherein Ar is α-cyano-3-phenoxy-benzyl.

21. A method of claim 17 wherein R is

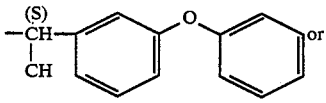 or

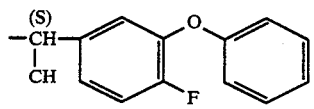

and the cyclopropane ring is in the 1R cis configuration.

22. A method of claim 17 wherein the active compound is selected from the group consisting of (S) α-cyano-3-phenoxy-benzyl 1R cis 2,2-dimethyl-3-[ΔE-2-fluoro-2-cyanoethenyl]cyclopropane carboxylate and the corresponding ΔZ isomer; (S) α-cyano-3-phenoxy-4-fluoro-benzyl 1R cis 2,2-dimethyl-3-[ΔE-2fluoro-2-cyanoethenyl]cyclopropane carboxylate and the corresponding ΔZ isomer; (R,S) cyano-2-(6-phenoxypyridyl)-methyl 1R cis 2,2-dimethyl-3[ΔE-2-fluoro-2-cyano-ethenyl]cyclopropane carboxylate and the corresponding ΔZ isomer.

23. A method of combatting insects comprising contacting insects with an insecticidally effective amount of at least one compound of claim 1.

24. A method of combatting nematodes comprising contacting nematodes with a nematocidally effective amount of at least one compound of claim 1.

25. A method of combatting acariens comprising contacting acariens with an acaricidally effective amount of at least one compound of claim 1.

26. A method of combatting affections caused by acariens in warm-blooded animals comprising contacting warm blooded animals with an anti-acarienly effective amount of at least one compound of claim 1.

* * * * *